_(12)_ United States Patent
Magri' et al.

(10) Patent No.: US 9,820,948 B2
(45) Date of Patent: Nov. 21, 2017

(54) LIPOIC ACID PELLET COMPOSITION

(75) Inventors: Paolo Magri', Mendrisio (CH);
Antonio Nardi, Segrate (IT); Annibale Salvi, Milan (IT); Flavio Villani, Milan (IT)

(73) Assignee: Olon S.p.A., Rodano (Milan) (IT)

( * ) Notice: Subject to any disclaimer, the term of this patent is extended or adjusted under 35 U.S.C. 154(b) by 0 days.

(21) Appl. No.: 12/739,449

(22) PCT Filed: Oct. 23, 2008

(86) PCT No.: PCT/IB2008/002835
§ 371 (c)(1),
(2), (4) Date: May 27, 2010

(87) PCT Pub. No.: WO2009/053824
PCT Pub. Date: Apr. 30, 2009

(65) Prior Publication Data
US 2011/0129442 A1    Jun. 2, 2011

(30) Foreign Application Priority Data
Oct. 23, 2007   (IT) .............................. MI2007A2051

(51) Int. Cl.
| A61K 31/385 | (2006.01) |
| A61K 9/48 | (2006.01) |
| A61K 31/202 | (2006.01) |
| A61K 9/50 | (2006.01) |

(52) U.S. Cl.
CPC .......... *A61K 9/4875* (2013.01); *A61K 9/4808* (2013.01); *A61K 31/202* (2013.01); *A61K 9/5078* (2013.01)

(58) Field of Classification Search
None
See application file for complete search history.

(56) References Cited

U.S. PATENT DOCUMENTS

| 6,479,069 | B1 | 11/2002 | Hamilton |
| 2005/0106247 | A1* | 5/2005 | Venkatesh ............ A61K 9/5078 424/469 |
| 2005/0181048 | A1* | 8/2005 | Romero ........................ 424/469 |
| 2006/0193789 | A1* | 8/2006 | Tamarkin et al. ............... 424/47 |
| 2006/0270625 | A1* | 11/2006 | Vinik et al. ..................... 514/52 |
| 2009/0117232 | A1* | 5/2009 | Boltri et al. .................... 426/89 |

FOREIGN PATENT DOCUMENTS

| EP | 1 325 747 | 7/2003 |
| WO | WO 99/61004 | 12/1999 |
| WO | WO 2004/041257 | 5/2004 |
| WO | WO 2006/089211 | 8/2006 |
| WO | WO 2007123284 A1 * | 11/2007 |
| WO | WO 2007138022 A2 * | 12/2007 |

OTHER PUBLICATIONS

Soybean Oil, available at <http://www.soya.be/soybean-oil.php>.*
"Reversal of Parenteral Nutrition-Associated Liver Disease in Two Infants with Short Bowel Syndrome Using Parenteral Fish Oil: Implications for Future Management," Gura, K., et al, Pediatrics 118: e197-e201 (2006).*
International Preliminary Report on Patentability in PCT/IB2008/002835 dated May 6, 2010.
International Search Report for PCT/162008/002835, dated Mar. 31, 2009.
Written Opinion of the International Searching Authority for PCT/162008/002835, dated Mar. 31, 2009.
Alleva, R. et al., "alpha-Lipoic acid supplementation inhibits oxidative damage, accelerating chronic would healing in patients undergoing hyperbaric oxygen therapy", Biochemical and Biophysical Research Communications, vol. 333, No. 2, (Jul. 29, 2005), pp. 404-410.

* cited by examiner

*Primary Examiner* — David J Blanchard
*Assistant Examiner* — Daniel F Coughlin
(74) *Attorney, Agent, or Firm* — Nixon & Vanderhye P.C.

(57) ABSTRACT

The present invention concerns a new composition based on pellets of lipoic acid in a lipophilic medium, if necessary combined with other active ingredients.

15 Claims, No Drawings

LIPOIC ACID PELLET COMPOSITION

This application is the U.S. national phase of International Application No. PCT/IB2008/002835 filed 23 Oct. 2008, which designated the U.S. and claims priority to IT Application No. MI2007A 002051 filed 23 Oct. 2007, the entire contents of each of which are hereby incorporated by reference.

The present invention concerns a new composition based on pellets of lipoic acid in a lipophilic medium, optionally in combination with other active ingredients.

PRIOR ART

Lipoic acid, 1,2-dithiolan-3-pentanoic acid, also known as thioctic acid, is an active ingredient with antioxidant activity and is used in the treatment of various pathologies, for example liver and biliary diseases, neuropathies of various origin, hypercholesterolemia, dyslipidemia, mushroom poisoning, cancer and others.

Lipoic acid has considerable formulation problems, due to its chemical-physical characteristics: it is a yellow powder with melting point 60-61° C., with characteristic and "aggressive" smell and flavour, and tends to polymerise by opening of the —S—S— bond, generating a sticky glue; it is practically insoluble in water and relatively soluble in ethanol.

It is therefore difficult to prepare stable pharmaceutical compositions comprising lipoic acid.

The patent application EP 1325747 concerns a dietary supplement based on numerous components including lipoic acid. In this document no pre-treatment of the lipoic acid is indicated and it is therefore used as is, in powder form. As already mentioned, the processing of lipoic acid is difficult due to the serious problems specified above and the stability of the compositions that contain it is not at all guaranteed. Moreover due to the numerous components contained in the supplement of the above application, interactions take place between the lipoic acid and the various components, and these interactions not only worsen the stability of the composition but also lead to the degradation of an important part of the lipoic acid with consequent drop in titre. The titre of lipoic acid was evaluated in a composition on the market representing the implementation of the product described and claimed in EP1325747 and the quantity of lipoic acid present was found to be lower than the quantity declared, proof of the fact that the composition is far from stable and that the lipoic acid present in it is subjected to degradation. Neither the nature nor the pharmacological effects of said degradation products are known.

The above-mentioned patent EP1325747 also describes combination of the lipoic acid with gamma-linolenic acid and selenium or its derivatives. The selenium or its derivatives are considered essential for the gastric tolerability of the composition. It was also noted that the concentration of the gamma-linolenic acid used is not indicated, and since it is known that said acid is commercially available as mixtures comprising said acid in various concentrations, for example from 9% w/w to approximately 40% w/w, the quantity of gamma-linolenic acid actually used in the compositions described is not understood.

Recently a patent application was filed by the present applicant (MI2006A001024-PCT/EP2007/055124) claiming new lipoic acid-based pellets, said pellets being coated so that they are stable and can be easily formulated and are therefore suitable for the preparation of pharmaceutical compositions or food and/or dietary preparations, for example.

The object of the present invention is to provide new lipoic acid-based compositions which overcome the drawbacks of the prior art, are easy to formulate and are stable in the long term.

A further object of the invention is to provide compositions based on combinations of lipoic acid and other active ingredients, stable in a lipophilic environment.

It has been found that the pellets containing lipoic acid in accordance with the patent applications MI2006A001024 and PCT/EP2007/055124 are particularly stable in lipophilic media. This observation has led the present inventors to search for a composition for oral administration comprising lipoic acid which is stable, easy to formulate and suitable for the combination of several active ingredients, avoiding interactions and chemical reactions between them and thus improving the stability of the composition.

DESCRIPTION OF THE INVENTION

Thus, according to one of its aspects, the invention concerns a composition comprising pellets of lipoic acid, or one of its salts, carried in at least one lipophilic medium.

The expression "pellets of lipoic acid" indicates, according to the present invention, particles consisting of an inert nucleus, coated with lipoic acid, in turn further coated by a first layer of insulating polymeric material and a second polymeric layer resistant to the gastric pH.

Said pellets are described in detail in the patent applications MI2006A001024 and PCT/EP2007/055124, filed on 25th May 2006 and 25th May 2007 respectively and incorporated here as a reference. Some details of said pellets are nevertheless provided also in the following description.

The lipoic acid according to the present invention is in racemic form or enantiomeric form R and/or S, in any degree of purity. Use of the mixtures of the two enantiomers, in any reciprocal proportion, is also included in the present invention.

According to the present invention, the salts of lipoic acid can also be used. In the present description, reference to the lipoic acid also includes its salts, provided that they are acceptable from the pharmaceutical and/or alimentary point of view. The quantities of lipoic acid indicated here refer to the non-salified, acidic form.

"Lipophilic medium" here indicates at least one vehicle or at least one lipophilic component, pharmaceutically acceptable or in any case edible. Mixtures of vehicles or lipophilic components can also be used.

According to a preferred aspect of the present invention, the lipophilic medium is a lipophilic component having beneficial properties for the human or animal organism, for example antioxidant properties or properties that regulate the metabolism of fats.

Alternatively, the lipophilic medium can be an inert medium, which must be pharmaceutically acceptable or in any case edible, the sole purpose of which is to act as a carrier for the pellets of lipoic acid and any other active ingredients and additives. If the lipophilic medium is an inert lipophilic component, for example an edible oil, the composition of the invention will preferably also comprise at least one other active ingredient.

"Active ingredient" here indicates a component, understood as a single molecule or a mixture of different molecules, having an activity beneficial for the organism, for example a drug or a nutraceutic component.

According to a preferred embodiment, the lipophilic medium comprises EPA ((5Z,8Z,11Z,14Z,17Z)-5,8,11,14, 17-eicosapentaenoic acid) and DHA ((4Z,7Z,10Z,13Z,16Z, 19Z)-4,7,10,13,16,19-docosaesaenoic acid). In this case the lipophilic medium can be either an inert lipophilic component, in any case pharmaceutically acceptable and edible, or a lipophilic medium which, by its very nature, comprises EPA and DHA.

According to a preferred embodiment, the lipophilic medium is fish oil or cod liver oil. Said oils can be purchased in a purified form and enriched in Omega 3 in particular in EPA and DHA.

Fish oil or cod liver oil contain polyunsaturated fatty acids, called Omega 3, including EPA and DHA.

According to a preferred embodiment, the lipophilic medium is the fish oil or the cod liver oil in a purified form and enriched in Omega 3, in particular enriched in EPA and DHA.

According to a particularly preferred embodiment, the lipophilic medium comprises EPA, DHA or in general Omega 3, in purified form.

According to another preferred embodiment, the lipophilic medium comprises linolenic acid, in particular gamma-linolenic acid. Gamma-linolenic acid is an essential fatty acid also called ALA or 18:3; ALA, also part of the Omega 3 family.

According to another embodiment the lipophilic medium comprises gamma-linolenic acid as the only other active ingredient (in addition to the lipoic acid) or in combination with other active ingredients mentioned above (EPA, DHA or, in general, Omega 3, fish oil or cod liver oil).

The expression "lipophilic medium which comprises gamma-linolenic acid" includes the oils derived from vegetable extracts rich in gamma-linolenic acid, such as borage oil and evening primrose oil, and others.

According to another preferred embodiment the lipophilic medium also comprises benfotiamine.

According to another preferred embodiment, the lipophilic medium comprises gamma-linolenic acid and also comprises benfotiamine.

The composition of the invention can also comprise other active ingredients, as defined above. Said further active ingredients can be in liquid or solid form.

With respect to the prior art, the invention offers the inestimable advantage of preventing the interaction between the lipoic acid, a highly reactive component which is difficult to process, and the lipophilic medium and any other components present. In fact, the pellets separate the lipoic acid from the other ingredients by creating a physical barrier.

Use of the pellets and the resulting physical separation of the lipoic acid from the rest of the composition furthermore allows the components of the formulation to be used at high purity and concentration.

In fact, the physical separation provided by the pellets permits the use of one or more lipophilic components with a high degree of purity, i.e. it is not necessary to disperse the components inside inert solid and/or liquid masses in order to limit the reciprocal interactions inside the composition.

For example, in the case of the gamma-linolenic acid, adopting the composition of the invention it is possible to use a gamma-linolenic acid contained in oils (usually natural extracts, for example of borage or evening primrose) at concentrations equal to the maximum purity currently available on the market (20% to 40% or more), with or without the addition of traces of stabilisers such as Vitamin E and Vitamin C.

The pellets of lipoic acid are also very useful in particular cases in which the possible combinations envisage the use of active ingredients available exclusively in liquid form and at relatively high concentrations. By way of example only, we can cite (in addition to the lipophilic components mentioned above, i.e. fish oils, DHA, EPA and gamma-linolenic acid): evening primrose oil, a natural source of gamma linolenic acid), conjugated linolenic acid, linseed oil, gamma-tocopherol, hempseed oil, the tocotrienols, and some vitamins.

It is to be understood that the use of components with high purity is fundamental for limiting the size of the dosage unit, in fact the size of the capsule should always be considered a critical parameter and using the composition of the invention, the greater the possibility of formulating active ingredients with high purity in conditions of comparable stability, the smaller the capsules that can be used, because liquid components at high purity permit the use of smaller capsules than those required to contain the same quantity of components when supported on inert carriers.

As said, the pellets of lipoic acid preferably used are those described in MI2006A001024 and PCT/EP2007/055124. Said pellets are preferably particles consisting of an inert nucleus, coated in lipoic acid, in turn further coated by a first layer of insulating polymeric material and a second polymeric layer resistant to the gastric pH.

Said inert nucleus consists preferably of sucrose, microcrystalline cellulose or other inert materials. The first polymeric layer is preferably formed of hydroxypropylmethylcellulose or hydroxypropylcellulose, while the second layer comprises one or more compounds chosen from esters of cellulose, polyvinylacetate phthalate, copolymers of methacrylic acid and esters of methylacrylate, cellulose acetate phthalate, hydroxypropylmethylcellulose phthalate, hydroxypropylmethylcellulose acetate phthalate, hydroxypropylmethylcellulose acetate succinate, Eudragit® and shellac. The details of the process for preparation of the pellets described above and various type of pellets that can be obtained are provided in the above-mentioned patent applications.

Advantageously the pellets contain from 5 to 60% of lipoic acid, preferably around 50% (w/w).

The size of the pellets used is also a fairly critical parameter as it is preferable to work with mean diameters of less than one millimeter (1000 microns), thus minimising the risk of a pellet being accidentally trapped in the gelatin wall during the closing phase, making it subject to rupture or loss of content. Advantageously, pellets with diameters of between 100 and 1000 microns are used, preferably between 300 and 600 microns.

The compositions of the invention are advantageously formulated in dosage units, for example in the form of gelatin capsules, hard or soft, the latter being particularly preferred.

The soft gelatin capsules are able to contain in a sealed protected environment all components that can be included in the matrix forming the capsule.

In general, the gelatin capsules can be filled, as is known in the art, by means of one or several filling systems simultaneously. In the first case, it is common practice to prepare suspensions and/or emulsions in which all the ingredients are uniformly dissolved or suspended before volumetric filling and dosing are performed, i.e. one single pump is used which loads the suspension of pellets and lipophilic medium plus any other substances, previously prepared and mixed to ensure uniformity, thus permitting the required volumetric dosage of the active ingredients.

Alternatively, when several filling systems are adopted, two separate lines can be used which load the oily component and the solid component (pellets or granules) respectively, synchronised to ensure the required dosage.

The dosage units according to the invention can contain, for example, from 10 to 1000 mg of lipoic acid, preferably from 100 to 800 mg, for example approximately 200, 300, 400, 500 or 600 mg.

The lipophilic medium can be contained in said dosage units in varying quantities, for example in the case of the capsules, according to the dimensions of the capsule if the lipophilic medium is inert or according to the concentration of active ingredients contained in it, in order to obtain the required dosage inside the capsule.

Consequently, when the lipophilic medium is a lipophilic component having beneficial properties for the human or animal organism, said component is present in the quantities normally used in conventional dietary and therapeutic practice. Said quantities can be administered in one single dosage unit or in several dosage units throughout the day.

As said, the use of pellets prevents interactions of the lipoic acid with the lipophilic component(s) which can thus be used in a particularly pure and effective form.

For example, when the lipophilic medium is fish oil or cod liver oil, said component can be present in quantities of between 100 and 1000 mg, preferably between 500 and 800 mg, for example 400-600 mg. Advantageously the fish oil or the cod liver oil will contain no less than 60% of EPA and DHA, in a varying reciprocal ratio, for example in a ratio of approximately 2:1.

When the lipophilic medium consists of Omega 3, substantially a mixture of EPA and DHA, it is present in quantities of between 100 and 3000 mg or even more.

When the lipophilic component comprises gamma linolenic acid, said component is used in quantities such that approximately 300-1000 mg, for example approximately 400-600 mg, for example approximately 500 mg of pure gamma linolenic acid are taken per day. Said quantity can be contained in one single dosage unit or split into several dosage units.

Said dosage units are preferably taken orally, once or several times a day.

In the composition of the invention, the pellets of lipoic acid are dispersed in the lipophilic medium, while maintaining their physical integrity, and the resulting composition is particularly stable. The composition obtained is therefore a mixture of pellets of lipoic acid and lipophilic medium (consisting of one or more lipophilic components).

According to a particularly preferred aspect, the invention concerns a composition in the form of gelatin capsules, preferably soft, comprising the pellets of lipoic acid or its salts, as defined above, and a lipophilic component chosen from fish oil, Omega 3 and their mixtures.

According to a further particularly preferred aspect, the invention concerns a composition in the form of a gelatin capsule, preferably soft, comprising the pellets of lipoic acid or its salts, as defined above, and a lipophilic component which is the gamma-linolenic acid, if necessary combined with benfotiamine.

Benfotiamine and any further solid active ingredients can be added by direct mixing in the composition of the invention. However, according to an advantageous embodiment of the present invention, the benfotiamine and any further solid active ingredients are used after granulation, if necessary in combination with inert additives, well known in the art. According to a preferred embodiment, granules are formed which have physical properties (bulk density, flowability, etc.) similar to those of the pellets of lipoic acid used in the composition of the invention. This allows an even stabler composition to be obtained which can be more easily homogenised.

The composition of the invention has an antioxidant effect and is useful for the treatment of oxidative stress and, in any case, all pathologies for which lipoic acid is indicated.

Use of the composition of the invention for the preparation of a medicament for the treatment of oxidative stress constitutes a further subject of the present invention.

The composition of the invention has proved to be effective and well tolerated, also in the absence of selenium or its derivatives.

The composition of the invention can also contain other active ingredients, in liquid or solid form, advantageously one or two further active ingredients, provided that they are stable in a lipophilic environment.

Due to the presence of the lipophilic medium, the interactions between the pellets of lipoic acid and any other active ingredients present are greatly reduced, with enormous advantages for the stability of the composition. The fact that the lipoic acid is in the form of coated pellets therefore further reduces the risk of interactions and degradation of the components. This obviously represents an important technical step forward in the formulation of active ingredients which, for example, have low stability, low solubility and/or are very reactive.

Said further active ingredients, in solid or liquid form, are for example chosen from among painkillers, drugs active in the treatment of diabetic neuropathies, hepatoprotectors, drugs active in the prevention of alcohol abuse, drugs active in supporting therapy for oxidative stress generated by chemotherapy, antagonists of angiotensin II, ACE inhibitors, antiviral drugs, antitumoral drugs and antidepressants provided, as said, that they are stable in a lipophilic environment.

Active ingredients can, for example, be chosen from gabapentin, pregabalin, olmesartan captopril, interferon, acamprosate and megestrol.

The compositions of the invention can also include components with antioxidant action, for example acetylcysteine, acetyl-1-carnitine, alpha-tocoferol (vitamin E) acetate, beta carotene, biotine, boron, chlorophyll, chrysin, *Lycopodium* and its extracts, cocoa flavonoids, coenzyme Q10, conjugated linolenic acid, copper, *Coptis chinensis* also called huang lian, curcuminoids, daidzeine, liquorice including its extracts devoid of glycyrrhizin, dimethyl sulfoxide, fish oils in general, (cod, herring, tuna, salmon, etc.) evening primrose oil (*Oenothera Biennis*, a natural source of gamma-linolenic acid), linseed oil, pholates, gamma-tocopherol, garlic, genisteine, germanium, ginseng, glucosamine, peptidic derivatives of glutamine, glutathione, glycine, glycitein, grapeseed oil, grape proantocyanidines, green tea catechins, extracts or parts of *Viola tricolor*, hempseed oil, hesperetin, hesperidin, hydroxyethylrutosides, indol-3-carbinol, inositol hexaphosphate, lactoferrine, lactulose, 1-arginine, 1-carnitine, 1-cysteine, 1-cystidine, 1-methionine, 1-theanine, lycopene, manganese, melatonin, extracts or parts of marian thistle (*Sylibum marianum*), nicotinamide, pantetine, pantothenic acid, propolis, pumpkin seeds, picnogenol (pine bark extract), pyruvate, quercitine, resveratrole, riboflavin vitamin B2, rutin, secoisolariciresinol, diglucoside (sdg), shark cartilage, soy isoflavones, soy proteins, spirulina, sulforaphane (derivative of glucoraphanin), taurine, thiamine (vitamin B1), tocotrienols, vinpocetine, vitamin A, vitamin B6, vitamin C, vitamin D, vitamin E, vitamin K, wheat/malt and their derivatives, serum proteins and zinc.

The compositions of the invention can also include the following components: L-alanine, L-arginine HCl, L-cystin, L-creatine, DL-phenylalanine, L-phenylalanine, L-glutamine, L-isoleucine, L-histidine, L-histidine HCl, L-leucine, L-lysine HCl, melatonin, L-ornithine, alpha ketoglutarate, L-ornithine HCl, L-proline, L-serine, L-tyrosine, L-tryptophan, L-valine, acetyl carnitine, propionyl carnitine, folic acid, lutein, zeaxanthin, rice oil, terpenes, tocopherols, tocotrienols, ginseng, gammaorizanol, polycosanols, ceramides, sennosides, polyvitamin complexes, sugars, maltodextrins, flavonoids, hesperidin, naringine, diosmine, hesperidin methyl chalcone, troxerutin, lycopene, resveratrole, hydrosmin and propolis.

The compositions of the invention can also contain the conventional additives and excipients known in the art, for example stabilising agents and suspending agents.

The dosage units comprising the composition of the invention constitute a further subject of the present invention.

The compositions and the dosage units of the invention are prepared according to the methods known to a person skilled in the art.

The compositions of the invention can be prepared by mixing the various components, for example adding the various components to the chosen lipophilic medium.

The dosage units according to the invention are prepared by using the composition of the invention according to the techniques well known in the art.

EXPERIMENTAL SECTION

Preparation 1

Preparation of the Lipoic Acid Pellets

Pellets of lipoic acid are prepared as described in MI2006A001024 and PCT/EP2007/055124.

In short, the pellets are prepared via the following stages:
(i) the lipoic acid is applied on inert nuclei, obtaining "active" nuclei;
(ii) a layer of polymeric insulating material is applied on said active nuclei;
(iii) a second polymeric layer is applied on the active coated nuclei obtained in stage (ii); and
(iv) the pellets thus obtained are dried and recovered.

Details of the materials used and the procedures are provided in the preceding description and in the above-mentioned patent applications.

In the following examples, pellets of lipoic acid containing 50% w/w of active ingredient (lipoic acid) are used.

Example 1

A soft gelatin capsule is prepared containing:

| | |
|---|---|
| lipoic acid in pellet form | 300 mg |
| fish oil | 500 mg |

Example 2

A soft gelatin capsule is prepared containing:

| | |
|---|---|
| lipoic acid in pellet form | 500 mg |
| fish oil | 800 mg |

Example 3

A soft gelatin capsule is prepared containing:

| | |
|---|---|
| lipoic acid in pellet form | 400 mg |
| Omega 3 | 2000 mg |

Example 4

A soft gelatin capsule is prepared containing:

| | |
|---|---|
| lipoic acid in pellet form | 300 mg |
| fish oil | 700 mg |
| gabapentin | 300 mg |

Example 5

A soft gelatin capsule is prepared containing:

| | |
|---|---|
| lipoic acid in pellet form | 300 mg |
| fish oil | 700 mg |
| pregabalin | 120 mg |

Example 6

A soft gelatin capsule is prepared containing:

| | |
|---|---|
| lipoic acid in pellet form | 300 mg |
| fish oil | 700 mg |
| gabapentin | 300 mg |
| coenzyme Q10 | 30 mg |

Example 7

A soft gelatin capsule is prepared containing:

| | |
|---|---|
| lipoic acid in pellet form | 200 mg |
| coenzyme Q10 | 30 mg |
| vegetable oil qs | |

In the following examples, pellets of lipoic acid containing 50% of active ingredient (lipoic acid) and a lipophilic medium containing gamma-linolenic acid at a concentration of 20 and 40% of active ingredient are used (all the concentrations are expressed w/w).

Example 8

A soft gelatin capsule is prepared containing:

| | |
|---|---|
| lipoic acid in pellet form | 300 mg |
| gamma-linolenic acid 40% | 312.5 mg |

Example 9

A soft gelatin capsule is prepared containing:

| | |
|---|---|
| lipoic acid in pellet form | 400 mg |
| gamma-linolenic acid 40% | 416 mg |
| stabilising and suspending agents: | qs |
| to be taken preferably 3 times a day | |

Example 10

A soft gelatin capsule is prepared containing:

| | |
|---|---|
| lipoic acid in pellet form | 300 mg |
| gamma-linolenic acid 20% | 625 mg |
| stabilising and suspending agents: | qs |
| to be taken preferably 4 times a day | |

Example 11

A soft gelatin capsule is prepared containing:

| | |
|---|---|
| lipoic acid in pellet form | 400 mg |
| gamma-linolenic acid 20% | 832 mg |
| stabilising and suspending agents: | qs |
| to be taken preferably 3 times a day | |

In the following examples pellets of lipoic acid containing 50% of active ingredient (lipoic acid), a lipophilic medium containing gamma-linolenic acid at a concentration of 20 and 40% of active ingredient and granules of benfotiamine having a concentration of 50 or 80% of active ingredient are used (all the concentrations are expressed w/w).

Example 12

A soft gelatin capsule is prepared containing:

| | |
|---|---|
| lipoic acid in pellet form | 300 mg |
| gamma-linolenic acid 40% | 312.5 mg |
| benfotiamine 80% | 62.5 mg |
| stabilising and suspending agents: | qs |
| to be taken preferably 4 times a day. | |

Example 13

A soft gelatin capsule is prepared containing:

| | |
|---|---|
| lipoic acid in pellet form | 400 mg |
| gamma-linolenic acid 40% | 416 mg |
| benfotiamine 80% | 83 mg |
| stabilising and suspending agents: | qs |
| to be taken preferably 3 times a day. | |

Example 14

A soft gelatin capsule is prepared containing:

| | |
|---|---|
| lipoic acid in pellet form | 300 mg |
| gamma-linolenic acid 20% | 625 mg |
| benfotiamine 50% | 100 mg |
| stabilising and suspending agents: | qs |
| to be taken preferably 4 times a day. | |

Example 15

A soft gelatin capsule is prepared containing:

| | |
|---|---|
| lipoic acid in pellet form | 400 mg |
| gamma-linolenic acid 40% | 832 mg |
| benfotiamine 80% | 133 mg |
| stabilising and suspending agents: | qs |
| to be taken preferably 3 times a day. | |

The invention claimed is:

1. A composition comprising pellets of lipoic acid, or one of its salts, carried in a lipophilic medium, wherein said pellets are particles consisting of an inert nucleus coated in (i) lipoic acid; (ii) a first layer of insulating polymeric material applied on said lipoic acid coating, wherein said first layer is hydroxypropylmethylcellulose or hydroxypropylcellulose; and (iii) a second polymeric layer resistant to gastric pH applied on said first layer, wherein said second layer comprises one or more compounds selected from the group consisting of esters of cellulose, polyvinylacetate phthalate, copolymers of methacrylic acid and esters of methylacrylate, cellulose acetate phthalate, hydroxypropylmethylcellulose phthalate, hydroxypropylmethylcellulose acetate phthalate, hydroxypropylmethylcellulose acetate succinate, copolymers of esters of acrylic and methacrylic acid, and shellac, wherein said lipophilic medium is a pharmaceutically acceptable component.

2. Composition as claimed in claim 1, wherein said lipophilic medium has anti-oxidant properties.

3. Composition as claimed in claim 1, wherein said lipophilic medium comprises (5Z,8Z,11Z,14Z,17Z)-5,8,11,14,17-eicosapentaenoic acid (EPA) and (4Z,7Z,10Z,13Z,16Z,19Z)-4,7,10,13,16,19-docosaesaenoic acid (DHA).

4. Composition as claimed in claim 1, wherein said lipophilic medium is fish oil or cod liver oil.

5. Composition as claimed in claim 4, wherein said lipophilic medium is fish oil or cod liver oil in a purified form and enriched in Omega 3 polyunsaturated fatty acids.

6. Composition as claimed in claim 5, wherein said lipophilic medium is enriched in EPA and DHA.

7. Composition as claimed in claim 1, wherein said lipophilic medium comprises gamma-linolenic acid.

8. Composition as claimed in claim 1, further comprising an active ingredient selected from the group consisting of gabapentin, pregabalin, olmesartan captopril, interferon, acamprosate and megestrol.

9. Composition as claimed in claim 1, further comprising benfotiamine.

10. The composition as claimed in claim 1, wherein a dosage unit comprises between 100 and 1000 mg of fish oil or cod liver oil in purified form.

11. The composition as claimed in claim 1, wherein a dosage unit comprises between 100 and 3000 mg of a mixture of EPA and DHA.

12. The composition as claimed in claim 1, wherein a dosage unit comprises 300-1000 mg of gamma-linolenic acid.

13. The omposition as claimed in claim 1, wherein a dosage unit further comprises an active ingredient selected from the group consisting of gabapentin, pregabalin, olmesartan captopril, interferon, acamprosate and megestrol.

14. Composition as claimed in claim 1, further comprising an active ingredient with antioxidant action.

15. A method for treatment of oxidative stress which comprises administering, to a subject in need thereof, a composition comprising pellets of lipoic acid, or one of its salts, carried in a lipophilic medium, wherein said pellets are particles consisting of an inert nucleus coated in (i) lipoic acid; (ii) a first layer of insulating polymeric material applied on said lipoic acid coating, wherein said first layer is hydroxypropylmethylcellulose or hydroxypropylcellulose; and (iii) a second polymeric layer resistant to gastric pH applied on said first layer, wherein said second layer comprises one or more compounds selected from the group consisting of esters of cellulose, polyvinylacetate phthalate, copolymers of methacrylic acid and esters of methylacrylate, cellulose acetate phthalate, hydroxypropylmethylcellulose phthalate, hydroxypropylmethylcellulose acetate phthalate, hydroxypropylmethylcellulose acetate succinate, copolymers of esters of acrylic and methacrylic acid, and shellac wherein said lipophilic medium is a pharmaceutically acceptable component.

* * * * *